(12) United States Patent
Suenaga et al.

(10) Patent No.: US 6,838,259 B2
(45) Date of Patent: Jan. 4, 2005

(54) PROCESS FOR PRODUCING KISS-1 PEPTIDE

(75) Inventors: Masato Suenaga, Yamaguchi (JP); Takao Yamada, Osaka (JP); Osamu Nishimura, Hyogo (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/168,050
(22) PCT Filed: Dec. 14, 2000
(86) PCT No.: PCT/JP00/08837
§ 371 (c)(1), (2), (4) Date: Jun. 13, 2002
(87) PCT Pub. No.: WO01/44469
PCT Pub. Date: Jun. 21, 2001

(65) Prior Publication Data
US 2003/0096956 A1 May 22, 2003

(30) Foreign Application Priority Data
Dec. 17, 1999 (JP) ............................................ 11-358693

(51) Int. Cl.⁷ .......................... C12P 21/02; C07K 19/00
(52) U.S. Cl. ...................... 435/69.1; 530/300; 530/350; 530/407
(58) Field of Search ........................ 435/69.1; 530/300, 530/350, 407

(56) References Cited

U.S. PATENT DOCUMENTS 6,103,882 A * 8/2000 Masato et al.

FOREIGN PATENT DOCUMENTS

| EP | 0 499 990 | 2/1992 |
|---|---|---|
| EP | 0 887 417 | 12/1998 |
| EP | 887417 | 12/1998 |
| WO | WO-97/13778 | * 4/1997 |
| WO | WO 98/39448 | 9/1998 |
| WO | WO 99/45942 | 9/1999 |

OTHER PUBLICATIONS

West, et al., "Chromosome Localization and Genomic Structure of the KiSS–1 Metastasis Suppressor Gene (Kiss1)", GENOMICS 54, 145–148 (1998), Article No. GE985566.

Lee, et al., "KiSS–1, a Novel Human Malignant Melanoma Metastasis–Suppressor Gene", Journal of the National Cancer Institute, vol. 88, No. 23, Dec. 4, 1996.

Hori, et al., *"Metastin Suppresses the Motility and Growth of CHO Cells Transfected with Its Receptor"*; Biochemical and Biophysical Research Communications, vol. 286, 958–963, 2001.

*A Novel Procedure for the preparation of biologically active recombinant peptides using a cyanylation reaction,* Koyama, N. et al, Journal of Biotechnology, vol. 32, No. 2, (1994), pp. 273–281.

* cited by examiner

*Primary Examiner*—Terry McKelvey
(74) *Attorney, Agent, or Firm*—Edwards & Angell, LLP; David G. Conlin; Marla L. Tocker

(57) ABSTRACT

A KiSS-1 peptide or a salt thereof can be produced in a large scale by subjecting a fusion protein or peptide in which a KiSS-1 peptide is ligated to the N-terminal of a protein or peptide having cysteine at the N-terminal, to the reaction of cleaving the peptide bond on the amino acid side of the cysteine residue.

11 Claims, 4 Drawing Sheets

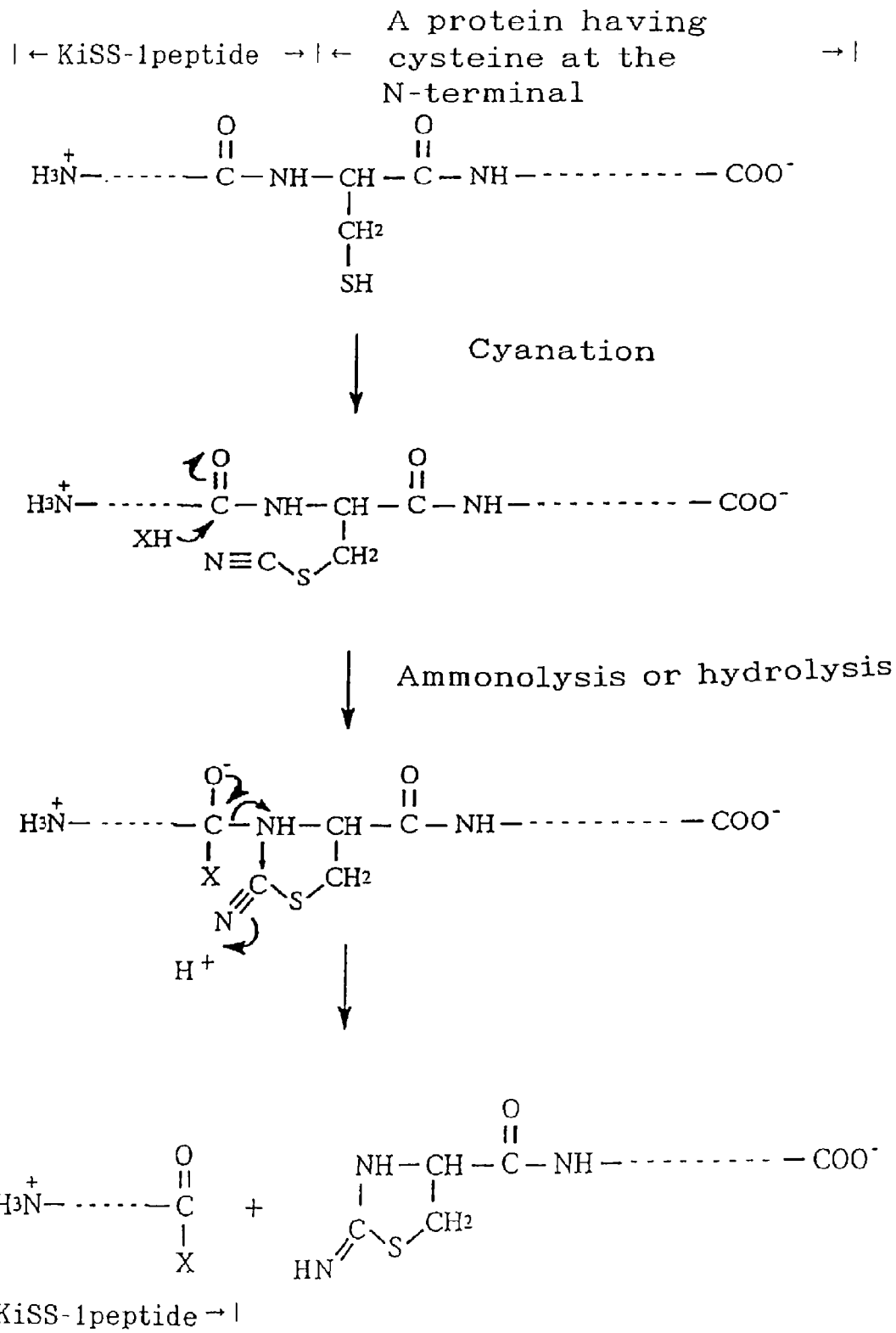

Fig.2

1    5'TATGGGTACTTCTCTGTCTCCGCCGCCGGAATCTTC

2
5'TGGTTCTCGTCAGCAGCCGGGTCTGTCTGCTCCGCACTCTCGTCA

3    5'GATCCCGGCTCCGCAGGGTGCTGTTCTGGTTCAGCGTGAAAA

4
5'AGACCTGCCGAACTACAACTGGAACTCTTTCGGTCTGCGTTTCTGCC

5
5'ACGAGAACCAGAAGATTCCGGCGGCGGAGACAGAGAAGTACCCATA

6
5'AGCCGGGATCTGACGAGAGTGCGGAGCAGACAGACCCGGCTGCTG

7
5'CGGCAGGTCTTTTTCACGCTGAACCAGAACAGCACCCTGCGG

8
5'TCGGGGCAGAAACGCAGACCGAAAGAGTTCCAGTTGTAGTT

US 6,838,259 B2

PROCESS FOR PRODUCING KISS-1 PEPTIDE

TECHNICAL FIELD

The present invention relates to a method of producing KISS-1 peptide or a salt thereof by preparing a fusion protein or polypeptide, and then subjecting said fusion protein or polypeptide to the reaction of cleaving the peptide bond.

BACKGROUND ART

When producing peptides using genetic recombinant technology, peptides are frequently expressed in the form of a fusion protein because peptides are prone to be decomposed inside the cell. Well-known methods of excising a target peptide from a fusion protein include chemical cleavage using bromcyan (Itakura, et al., Science, 198, 1056 (1977)), and enzymatic cleavage using factor Xa (Nagai, et. al., Methods in Enzymology, 153, 46(1987)).

Further, a well-known method of cleaving the peptide bond in a protein is to cleave the acyl cysteine bond using 2-nitro-5-thiocyanobenzoic acid ("Course on Biochemical Experiments" 1, Protein Chemistry II, Japan Biochemistry Society, ed., published by Tokyo Chemists, pp 247–250, 1976). Nonetheless, there has been no disclosure on excision of a target peptide from a protein.

When excising a target peptide from a fusion protein using conventional technology, the excision with bromcyan cannot be applied to the production of a peptide containing methionine, and has many problems on the yield of excision, etc.

In this way, it is desirable to have a method of efficiently cleaving a target peptide from a fusion protein or polypeptide.

SUMMARY OF THE INVENTION

As a result of researching in detail on a method of efficiently producing KiSS-1 peptide or a salt thereof, which is a new biologically active peptide, the present inventors discovered that KiSS-1 peptide or a salt thereof can be efficiently produced by preparing a fusion protein or polypeptide, in which a KiSS-1 peptide is ligated to the N-terminal of a protein or polypeptide having cysteine at the N-terminal, and then subjecting the fusion protein or polypeptide to the reaction of cleaving the peptide bond.

Thus, the present invention provides:

(1) a method of producing a KiSS-1 peptide or a salt thereof, which comprises subjecting a fusion protein, polypeptide or a salt thereof in which a KiSS-1 peptide is ligated to the N-terminal of a protein or peptide having cysteine at the N-terminal, to the reaction of cleaving the peptide bond on the amino group side of said cysteine residue;

(2) a method of producing a KiSS-1 peptide or a salt thereof, which comprises expressing a fusion protein, polypeptide or a salt thereof in which a KiSS-1 peptide is ligated to the N-terminal of a protein or peptide having cysteine at the N-terminal by culturing a transformant having a vector comprising DNA encoding the fusion protein or polypeptide; and subjecting the expressed fusion protein, polypeptide or the salt thereof to the reaction of cleaving the peptide bond on the amino group side of said cysteine residue;

(3) a producing method described in item (1) or (2) wherein the C-terminal of the KiSS-1 peptide is an amide;

(4) a producing method described in item (1) or (2) wherein the cleavage reaction is S-cyanation reaction followed by an ammonolysis or hydrolysis reaction;

(5) a producing method described in item (1) or (2) wherein the KiSS-1 peptide is a peptide comprising an amino acid sequence represented by SEQ ID NO: 1;

(6) a producing method described in item (1) or (2) wherein the KiSS-1 peptide is (i) a peptide having the amino acid sequence from the $40^{th}$ to $54^{th}$ residues from the N-terminal of the amino acid sequence represented by SEQ ID NO: 1; (ii) a peptide having the amino acid sequence from the $45^{th}$ to $54^{th}$ residues from the N-terminal of the amino acid sequence represented by SEQ ID NO: 1; (iii) a peptide having the amino acid sequence from the $46^{th}$ to $54^{th}$ residues from the N-terminal of the amino acid sequence represented by SEQ ID NO: 1; or (iv) a peptide having the amino acid sequence from the $47^{th}$ to $54^{th}$ residues from the N-terminal of the amino acid sequence represented by SEQ ID NO: 1;

(7) a producing method described in item (1) or (2) wherein the protein or peptide having cysteine at the N-terminal is any of the following having cysteine at the N-terminal: interferon, interleukin, fibroblast growth factor, (pro)urokinase, lymphotoxin, tumor necrosis factor (TNF), β-galactosidase, storage proteins, streptoavidine, protein A, protein G, tissue plasminogen activator (TPA), or muteins or fragments thereof;

(8) a producing method described in item (1) or (2) wherein the protein or peptide having cysteine at the N-terminal is a protein or peptide that comprises an amino acid sequence represented by SEQ ID NO: 3 and has a cysteine residue added to the N-terminal;

(9) a producing method described in item (1) or (2) wherein the protein or peptide having cysteine at the N-terminal is a protein that comprises an amino acid sequence represented by SEQ ID NO: 3 and has a cysteine residue added to the N-terminal; the KiSS-1 peptide is a peptide having an amino acid sequence represented by SEQ ID NO: 1; and the KiSS-1 peptide to be produced is a peptide having an amino acid sequence represented by SEQ ID NO: 1 with an amide form of the C-terminal;

(10) a fusion protein, polypeptide or a salt thereof, in which KiSS-1 peptide is ligated to the N-terminal of a protein or peptide having cysteine at the N-terminal;

(11) a fusion protein, polypeptide or a salt thereof described in item (10), in which a KiSS-1 peptide comprising an amino acid sequence represented by SEQ ID NO: 1 is ligated to the N-terminal of a protein comprising an amino acid sequence represented by SEQ ID NO: 3 and having a cysteine residue added to the N-terminal;

(12) DNA comprising DNA encoding the fusion protein or peptide described in item (10);

(13) DNA described in item (12), which has: (i) a nucleic acid sequence represented by SEQ ID NO: 4; or (ii) a nucleic acid sequence represented by SEQ ID NO: 5;

(14) a vector comprising the DNA described in item (12);

(15) a transformant having the vector described in item (14); and

(16) *Escherichia coli* MM294 (DE3)/pTFC-KiSS-1 identified as FERM BP-6907.

Further, the present invention provides:

(17) a producing method described in item (2), comprising the following steps (i) to (iv):

(i) producing a DNA encoding a fusion protein or peptide in which a KiSS-1 peptide is ligated to the N-terminal cysteine of a protein or peptide having cysteine at the N-terminal, (ii) producing a vector comprising said DNA, (iii) expressing the fusion protein, peptide or salt thereof by culturing a transformant having said vector, and (iv) subjecting the expressed fusion protein, peptide or salt thereof to the reaction of cleaving the peptide bond on the amino group side of said cysteine residue.

BRIEF DESCRIPTION OF THE DRAWINGS

FIG. 1 indicates the reaction mechanism in the process of the present invention.

FIG. 2 indicates the DNA fragments used in Example 1, SEQ ID NOS: 7–14.

BEST MODE FOR CARRYING OUT THE INVENTION

Figure 3:
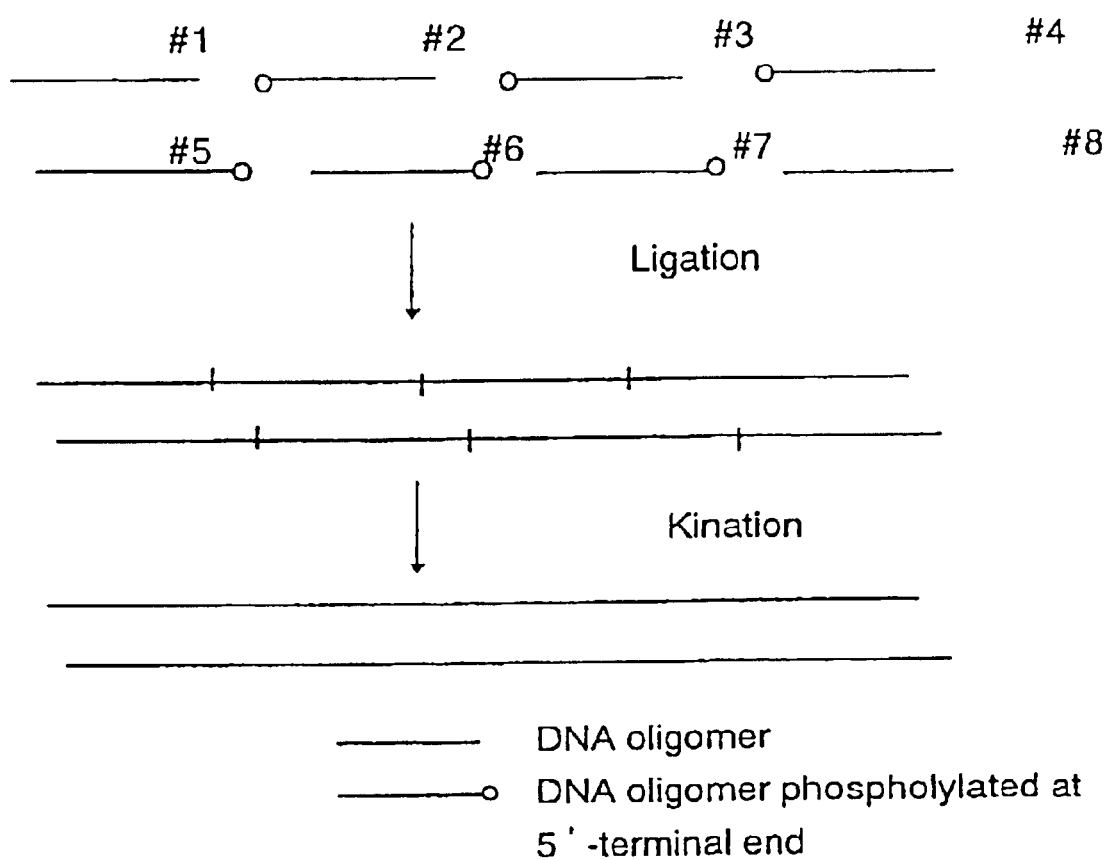
FIG. 3 indicates a schematic diagram of the production of the human KiSS-1 peptide using the double strand construct obtained in Example 1.

The KiSS-1 peptide used in the method of the present invention includes, for example, the human KiSS-1 peptide described in WO00/24890 (International Patent Application No. PCT/JP99/05905), and specifically, a peptide that contains the 47$^{th}$ to 54$^{th}$ residues from the N-terminal of the amino acid sequence represented by SEQ ID NO: 1, and consists of 8 to 54 amino acids.

"The peptide that contains the 47$^{th}$ to 54$^{th}$ residues from the N-terminal of the amino acid sequence represented by SEQ ID NO: 1, and consists of 8 to 54 amino acids" may be selected from any peptides which contain the 47$^{th}$ to 54$^{th}$ residues from the N-terminal of the amino acid sequence represented by SEQ ID NO: 1 and consists of 8 to 54 amino acids. However, this means that the peptide activity (for example, binding activity between the peptide and its receptor, or cell stimulation activity on the cell expressing the receptor caused by the peptide, etc.) is retained to the substantially same extent. Specifically, the following may be used: (i) the peptide having the amino acid sequence represented by SEQ ID NO: 1; and (ii) peptides comprising the 47$^{th}$ to 54$^{th}$ residues from the N-terminal of the amino acid sequence represented by SEQ ID NO: 1 at the C-terminal portion, and consisting of 8 to 15 amino acids.

More specifically, the following may be used as the KiSS-1 peptide: (i) the peptide having the amino acid sequence represented by SEQ ID NO: 1; (ii) the peptide having the 40$^{th}$ to 54$^{th}$ residues from the N-terminal of the amino acid sequence represented by SEQ ID NO: 1; (iii) the peptide having the 45$^{th}$ to 54$^{th}$ residues from the N-terminal of the amino acid sequence represented by SEQ ID NO: 1; (iv) the peptide having the 46$^{th}$ to 54$^{th}$ residues from the N-terminal of the amino acid sequence represented by SEQ ID NO: 1; and (v) the peptide having the 47$^{th}$ to 54$^{th}$ residues from the N-terminal of the amino acid sequence represented by SEQ ID NO: 1.

The above-mentioned KiSS-1 peptides have ligand activity in relation to the receptor protein OT7T175 described in WO00/24890 (International Patent Application No. PCT/JP99/05905).

In the peptides of the present specification, according to the conventional denotation, the N-terminal (amino terminal) is placed on the left side and the C-terminal (carboxyl terminal) on the right side. The C-terminal of the peptide represented by SEQ ID NO: 1 may be amide (—CONH$_2$), carboxyl group (—COOH), carboxylate (—COO$^-$), alkylamide (—CONHR), or ester (—COOR). R of the ester or alkylamide includes, for example, C$_{1-6}$ alkyl group such as methyl, ethyl, n-propyl, isopropyl, or n-butyl; a C$_{3-8}$ cycloalkyl group such as cyclopenthyl, or cyclohexyl; a C$_{6-12}$ aryl group such as phenyl, or α-naphthyl; a phenyl-C$_{1-2}$ alkyl such as benzyl, phenethyl, or benzhydryl; or a C$_{7-14}$ aralkyl group such as an α-naphthyl-C$_{1-2}$ alkyl, such as α-naphthylmethyl; or a pivaloyloxymethyl group generally used as an oral ester.

Salts of the KiSS-1 peptide of the present invention may be salts with physiologically acceptable bases (for example, alkali metals, etc.) and acids (organic acids, inorganic acids), and physiologically acceptable acid added salts are preferable. Such salts includes, for example, ones with inorganic acids (for example, hydrochloric acid, phosphoric acid, hydrobromic acid, sulfuric acid), or with organic acids (for example, acetic acid, formic acid, propionic acid, fumaric acid, maleic acid, succinic acid, tartinic acid, citric acid, malic acid, oxalic acid, benzoic acid, methane sulfonic acid, benzene sulfonic acid).

In the method of the present invention, the proteins or peptides having cysteine at the N-terminal are not limited. If there is no cysteine at the N-terminal, a protein or peptide may be given cysteine at the N-terminal using well-known methods.

The protein or peptide having cysteine at the N-terminal preferably has a molecular weight of 100 to 100,000, and more preferably a molecular weight of 300 to 50,000. In addition, the protein or peptide having cysteine at the N-terminal preferably has 1 to 1,000 amino acids, and more preferably 3 to 500 amino acids.

The above-mentioned proteins or peptides includes for example, interferon, interleukin, various growth factors such as fibroblast growth factor (aFGF, bFGF, etc.), (pro) urokinase, lymphotoxin, tumor necrosis factor (TNF), oxygen proteins such as β-galactosidase, storage proteins, streptoavisine; protein A, protein G, tissue plasminogen activator (TPA), or muteins or fragments thereof. Among those, fibroblast growth factors (aFGF, bFGF, etc.), or the muteins thereof, or a part thereof (a fragment) (for example, bFGF CS23 mutein, etc.) are preferably used.

An example of a bFGF CS23 mutein is a protein that comprises the following amino acid sequence:

Pro-Ala-Leu-Pro-Glu-Asp-Gly-Gly-Ser-Gly-Ala-Phe-Pro-Pro-Gly-His-Phe-Lys-Asp-Pro-Lys-Arg-Leu-Tyr-Cys-Lys-Asn-Gly-Gly-Phe-Phe-Leu-Arg-Ile-His-Pro-Asp-Gly-Arg-Val-Asp-Gly-Val-Arg-Glu-Lys-Ser-Asp-Pro-His-Ile-Lys-Leu-Gln-Leu-Gln-Ala-Glu-Glu-Arg-Gly-Val-Val-Ser-Ile-Lys-Gly-Val-Ser-Ala-Asn-Arg-Tyr-Leu-Ala-Met-Lys-Glu-Asp-Gly-Arg-Leu-Leu-Ala-Ser-Lys-Ser-Val-Thr-Asp-Glu-Cys-Phe-Phe-Phe-Glu-Arg-Leu-Glu-Ser-Asn-Asn-Tyr-Asn-Thr-Tyr-Arg-Ser-Arg-Lys-Tyr-Thr-Ser-Trp-Tyr Val-Ala-Leu-Lys-Arg-Thr-Gly-Gln-Tyr-Lys-Leu-Gly-Ser-Lys-Thr-Gly-Pro-Gly-Gln-Lys-Ala-Ile-Leu-Phe-Leu-Pro-Met-Ser-Ala-Lys-Ser (sequence No. 3); and that has a cysteine residue added to the N-terminal.

Regarding the DNA encoding the fusion protein (including fusion peptides) used in the method of the present invention, (1) the entire nucleic acid sequence may be chemically synthesized; (2) said DNA may be constructed by adding the nucleic acid sequence encoding cysteine to the N-terminal of the nucleic acid sequence encoding a protein, and then adding the nucleic acid sequence encoding the KiSS-1 peptide to the N-terminal; or (3) to obtain a fragment of said peptide, the DNA may be constructed using a technique such as site-directed mutagenesis for substituting the amino acid residue immediately after the desired fragment with cysteine.

In the above producing method (1), the well-known methods, for example, phosphoamidide method, triester phosphate method, diester method, or hydrogen phosphonate method may be used. A protein or peptide of short lenght may be synthesized completely at once, and a protein or peptide of long length may be produced by synthesizing parts and ligating the parts using T4DNA ligase.

In the aboveproducing method (2), the DNA encoding the protein on the C-terminal side is obtained by excising the DNA from chromosomes or cDNA with a suitable restriction enzyme and then subcloning into a vector; or cDNA is obtained. Subsequently, the DNA is cleaved with an appropriate restriction enzyme so that the protein has cysteine at the N-terminal, or a synthetic DNA is ligated to 5'-terminal of the DNA encoding the protein or a part thereof so that the protein is modified to have cysteine at the N-terminal. The DNA encoding the target protein (chemically synthesized, or cloned from an organism) is ligated to the 5'-terminal.

Examples of the DNA encoding the fusion protein obtained in the above manner includes DNAs represented by the following formula:

CGTACTTCTCTGTCTCCGCCGCCGGAATCTTCTGGTTCTCGTCAGCAGCC

GGTCTGTCTGCTCCGCACTCTCGTCAGATCCCGGCTCCGCAGGGTGCTGT

TCTGGTTCAGCGTGAAAAAGACCTGCCGAACTACAACTGGAACTCTTTCG

GTCTGCGTTTC-TGC or TGT-R (I)

(In the formula, R indicates the following nucleic acid sequence:

CCCGAGGATGGCGGCAGCGGCGCCTTCCCGCCCGGCCACTTCAAGGACCC

CAAGCGGCTGTACTGCAAAAACGGGGCTTCTTCCTGCGCATCCACCCCG

ACGGCCGAGTTGACGGGGTCCGGGAGAAGAGCGACCCTCACATCAAGCTA

CAACTTCAAGCAGAAGAGAGGAGTTGTGTCTATCAAAGGAGTGAGCGC

TAATCGTTACCTGGCTATGAAGGAAGATGGAAGATTACTAGCTTCTAAGT

CTGTTACGGATGAGTGTTTCTTTTTTGAACGATTGGAATCTAATAACTAC

AATACTTACCGGTCAAGGAAATACACCAGTTGGTATGTGGCACTGAAACG

AACTGGGCAGTATAAACTTGGATCCAAAACAGGACCTGGGCAGAAAGCTA

TACTTTTTCTTCCAATGTCTGCTAAGAGCTGC (fragment of bFGFCS23 mutein).

The above formula (I) means that the nucleic acid sequence: represented by R is ligated to the DNA sequence (SEQ ID NO: 2) encoding a peptide comprising a human KiSS-1 peptide through the nucleic acid sequence encoding cysteine.

The DNA encoding a KiSS-1 peptide may also be produced according to a well-known method using DNA represented by formula (I), or DNA encoding a KiSS-1 peptide mature form represented by SEQ ID NO: 15, or modified DNA thereof (for example, J. Natl. Cancer Inst., 88, 1731, 1996; WO98/39448).

DNA (plasmid) having ATG on the 5'-terminal, a downstream region encoding the aforementioned fusion protein and a translation termination codon, can be produced by chemical synthesis or by processing a cDNA encoding a well-known protein, which is prepared by genetic engineering, or by processing a DNA encoding the aforementioned proteins, which is derived from chromosomes.

In the present invention, the DNA encoding the fusion protein or peptides in which KiSS-1 peptide is bound to the N-terminal of the protein having cysteine at the N-terminal can be modified to encode the desired mutein by using conventional DNA technology, for example, site directed mutagenesis technology.

Site directed mutagenesis technology is well known, and is described in R. F. Lather, J. P. Lecoq: Genetic Engineering Academic Press (1983), pp 1–50. Mutagenesis directed by oligonucleotides is described in M. Smith, S. Gillam: Genetic Engineering: Principles and Method, Plenum Press (1981), Vol. 3, pp. 1–32.

To produce a plasmid having a DNA region encoding the aforementioned fusion proteins, a plasmid vector derived from *Escherichia Coli*, for example, pBR322 (Gene 2, 95(1977)), pBR313 (Gene 2, 75(1977)), pBR324, pBR325 (Gene 4, 124(1978)), pBR327, pBR328 (Gene 9, 287 (1980)), pBR329 (Gene 17, 79(1982)), pKY2289 (Gene 3, 1(1978)), pKY2700 (Biochemistry 52, 770(1980)), pACYC177, pACYC184 (Journal of Bacteriology, 134, 1141 (1978)), pRK248, pRK646, pDF (Methods in Enzymology, 68, 268(1979)), and pUC18, pUC19 (Yanischperon, et al: Gene, 33, 103(1985)) may be used. In addition, the following vectors may also be used: vectors using bacteriophages, such as λgt-vectors using λ-phage, for example, λgt-λC (Proc. Natl. Acad. Sci. U.S.A. 71, 4579 (1974)), λgt-λB (Proc. Natl. Acad. Sci. U.S.A. 72, 3461 (1975)), λDam (Gene, 1, 255(1977)), and Shalon vector (Science, 196, 161(1977); Journal of Virology, 29, 555 (1979)); and mp-vectors using filamentous phage, for example, mp18, mp19 (Yanishperon et al, Gene, 33, 103 (1985).

The above DNA preferably has a promoter upstream of the ATG, and said promoter may be any promoter suitable for the host used in the production of a transformant.

For example, for *Escherichia coli*, trp promoter, lac promoter, rec promoter, λ promoter, lpp promoter, and T7 promoter, etc.; for *Bacillus subtilis*, SP01 promoter, SP02 promoter, and penP promoter; for *Saccharomyces cerevisiae*, PHO5 promoter, PGK promoter, GAP promoter, and ADH promoter; and for animal cells, promoters derived from SV40, may be used. The SD (Shine and Delgarno) sequence may be inserted downstream of the promoter if necessary.

When using T7 promoter system, any of 17 different T7 promoters located on T7 DNA (J. L. Oakley et al.,: Proc. Natl. Acad. Sci., U.S.A., 74: 4266–4270 (1977), M. D. Rosa, Cell, 16: 815–825 (1979), N. Panayotatos, et al., Nature, 280 : 35 (1979), J. J. Dunn et al., J. Mol. Biol., 166: 477–535 (1983)) may be used as the T7 promoter. φ10 promoter (A. H. Rosenberg et. al., Gene, 56: 125–135 (1987) is preferred.

As the transcription terminator, a terminator that functions in *Escherichia* strains, preferably Tφ terminator (F. W. Studier et. al., J. Mol. Biol., 189: 113–130 (1986)) may be used.

Genes for a T7 RNA polymerase include T7 Gene (F. W. Studier et. al., J. Mol. Biol., 189: 113–130 (1986)).

The vector is preferably constructed by incorporating T7 promoter and T7 terminator into the aforementioned vector. Such a vector includes pET-1, pET-2, pET-3, pET-4, pET-5 (A. H. Rosenberg, Gene 56: 125–135 (1987), and pTB960-2 (EP-A-499990)), but pTB960-2 is preferably used.

The transformant of the present invention can be produced by transforming a host with the plasmid for expression obtained by the aforementioned method, using a well-known method (example, S. N. Cohen, et al, Proceedings of the National Academy of Science (U.S.A.), 69, 2110 (1972)).

Microorganism hosts to be transformed include *Escherichia* bacteria, *Bacillus* bacteria, yeast, and animal cells.

Said *Escherichia* bacteria include *Escherichia coli* (*E. coli*), specifically, *E. coli* K12H1 (Proceedings of the National Academy of Science (U.S.A.), 60, 160 (1968)), JM-103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), N4830 (Cell, 25, 713 (1981)), K-12MM294 (Proceedings of the National Academy of Science (U.S.A.), 73, 4174 (1976)) BL-21.

Said *bacillus* bacteria include *Bacillus subtilis*, specifically, *Bacillus subtilis* MI114 (Gene, 24, 255 (1983)), and 207–21 (Journal of Biochemistry), 95, 87 (1984)).

Said yeast includes *Saccharomyces cerevisiae*, specifically, *Saccharomyces cerevisiae* AH22 (Proceedings of the National Academy of Science (U.S.A.), 75, 1929 (1978)), XSB5 2–23C (Proceedings of the National Academy of Science (U.S.A.), 77, 2173 (1980)), BH-641A (ATCC28339), 20B-12 (Genetics, 85, 23 (1976)), and GM3C-2 (Proceedings of the National Academy of Science (U.S.A.), 78, 2258 (1981)).

Said animal cells includes Monkey cell COS-7 (Cell, 23, 175 (1981)), Vero (Nihon Rinshou [Japan Clinic] 21, 1209 (1963)), Chinese hamster cells CHO (Journal of Experimental Medicine, 108, 945 (1985)), mouse L cells (Journal of National Cancer Institute, 4, 165 (1943)), human FL cells (Proceedings of the Society of Experimental Biology and Medicine, 94, 532 (1957)), and hamster C cells, etc.

When utilizing T7 promoter system, an *E.coli* strain having T7 RNA polymerase genes (T7 gene 1) (F. W. Studier et al.: Journal of Molecular Biology, 189: 113–130 (1986)) may be used as the host for transformantion, which includes, for example, *E.coli* MM294, DH-1, C600, JM109, BL21. Alternatively, an *E.coli* strain having T7 RNA polymerase genes (T7 gene 1) in combination with another plasmid may also be used. Preferably, MM294 starin or BL21 strain is used in which a λ phage having a T7 gene 1 is lysogenized. In this case, the promoter for T7 gene 1 may be lac promoter, the expression of which is induced by isopropyl-1-thio-β-D-galactopyranoside (IPTG).

The transformation of *Escherichia* bacteria can be carried out according to, for example, methods described in the Proceedings of the National Academy of Science of the USA, vol. 69, 2110 (1972), and Gene, vol. 17, 107 (1982).

The transformation of *Bacillus* bacteria hosts can be carried out according to a well-known method, such as one described in Molecular and General Genetics, 168, 111 (1979).

The transformation of yeast hosts can be carried out according to a well-known method, such as one described in the Proceedings of the National Academy of Science of the USA, 75, 1929 (1978).

The transformation of animal cell hosts can be carried out according to a well-known method, such as one described in the Virology, 52, 456 (1973).

The fusion protein can be produced by culturing the above-described transformant in a medium, and collecting the fusion protein produced. A culture medium with a pH of approximately 6 to 8 is desirable.

M9 medium containing glucose and casamino acid (Journal of Experiments in Molecular Genetics, 431–433, Cold Spring Harbor Laboratory, New York, 1972)), etc. is preferable as the medium for culturing *Escherichia* bacteria. Agents such as 3β-indolyl acrylate or isopropyl β-D-thiogalactopyranside (IPTG) may be added to the medium in order to increase the efficiency of the promoter, if necessary.

If the host is *Escherichia* bacteria, culturing is normally conducted at approximately 15 to 43° C. for approximately 3 to 24 hours, and aeration and agitation may be applied if necessary.

If the host is *Bacillus* bacteria, culturing is normally conducted at approximately 30 to 40° C. for approximately 6 to 24 hours, and aeration and agitation may be applied if necessary.

When culturing a yeast transformant, for example, Burkholder minimum medium (Bostian, K. L. et al., Proceedings of the National Academy of Science, U.S.A., 77, 4505 (1980)) may be used. It is preferable to adjust the pH of the culture medium to approximately 5 to 8. Culturing is normally conducted at approximately 20 to 35° C. for approximately 24 to 72 hours, and aeration and agitation may be applied if necessary.

When culturing an animal cell transformant, MEM medium (Science, 122, 501 (1952)), DME medium (Virology, 8, 396 (1959)), RPMI 1640 medium (The Journal of the American Medical Association, 199, 519 (1967)), and 199 medium (Proceedings of the Society for Biological Medicine, 73, 1 (1950)) containing approximately 0.2 to 20%, preferably approximately 5 to 20% fetal bovine serum may be used. The pH is preferably approximately 6 to 8. Culturing is normally conducted at approximately 30 to 40° C. for approximately 15 to 60 hours, and aeration and agitation may be applied if necessary.

The fusion protein can be produced by culturing the aforementioned transformants, expressing and accumulating the aforementioned fusion protein in the culture medium, and then harvesting it.

M9 medium including glucose and casamino acid (J. Miller, Experiments in Molecular Genetics, 431–433 (Cold Spring Harbor Laboratory, New York 1972)), 2XYT medium (Messing, Methods in Enzymology, 101, 20 (1983)) LB medium may be used for culture media.

Culturing is normally conducted at approximately 15 to 43° C. for approximately 3 to 24 hours, and aeration and agitation may be applied if necessary.

When using a recombinant having a λcI-ts repressor and an expression vector having λPL-promoter, culturing is conducted at a temperature of 15 to 36° C., preferably approximately 30 to 36° C., and it is preferable to inactivate the λcI-ts repressor at approximately 37 to 42° C. In addition, in order to work the recA promoter more efficiently, i.e. to reduce the inhibitory function of the recA gene expression, opptionally, agents such as mitomycin C and nalidixic acid may be added, the medium may be irradiated with ultraviolet light, or the pH of the medium may be changed to alkali side.

When using T7 promoter sysytem, (1) TPTG, etc. is added if expressing a T7 gene (RNA polymerase gene) ligated downstream of the lac promoter; or (2) the temperature of the culture medium is increased, if expressing T7 gene (RNA polymerase gene) ligated downstream of the XPL-promoter. As the result, the expressed T7 phage RNA polymerase 1 specifically acts on the T7 promoter.

After culturing, the bacteria are collected by a well-known method, suspended in buffer solution, etc., and then crushed by treating with a protein denaturing agent, ultrasonication, enzymes such as lysozyme, glass bead, French press, or freeze-thawing. The supernatant is obtained by a well-known method, such as centrifugation.

Conventional protein purification methods may be employed to isolate the fusion protein from the supernatant obtained above. An appropriate combination of, for example, gel filteration, ion-exchange chromatography, absorption chromatography, high speed liquid chromatography, affinity chromatography, hydrophobic chromatography, or electrophoresis may be used In addition, the aforementioned fusion protein may be used in the next reaction process without purification, or with partial purification.

Next, the fusion protein and peptide obtained in this way are subjected to the reaction of cleaving the peptide bond on the amino group side of the cysteine residue. The aforementioned cleavage reaction may be, for example, S-cyanation reaction which is followed by a hydrolysis reaction. If an amide form of KiSS-1 peptide or salt thereof is desired as the final product, the S-cyanation reaction is followed by ammonolysis for the cleavage reaction. The S-cyanation reaction is conducted by reacting an S-cyanation reagent with the source material.

S-cyanation reagents include 2-nitro-5-thiocyanobenzoic acid (NTCB), 1-cyano-4-dimethyl aminopyridinium salts (DMAP-CN), and CN ions. The used amount of the S-cyanation reagents may be approximately 2 to 50 times to the total amount of thiol group in mole, and preferably approximately 5 to 10 times.

The reaction temperature may be between approximately 0 and 80° C., and preferably between approximately 0 and 50° C. Any buffer solution may be used as the solvent as long as it does not react with the S-cyanation reagent, including tris-hydrochloride buffer solution, tris-acetate buffer solution, phosphate buffer solution, and borate buffer solution. An organic solvent may be furhter contained as long as it does not react with the S-cyanation reagent.

The cleavage reaction may be carried out at a pH of 1 to 12. In particular, pH 7 to 10 is preferable when using NTCB, and pH 2 to 7 is preferable when using DMAP-CN in order to prevent an S—S exchange reaction. The reaction solution may further contain a denaturing agent such as guanidine hydrochloride.

Alkali treatment may be carried out for the aforementioned ammonolysis or hydrolysis reaction. The alkali treatment is conducted by adjusting the pH of an aqueous solution containing the source material to 7 to 14.

The pH adjustment is conducted by adding a suitable amount of a solution of ammonia, sodium hydroxide, amino compound (to be described later), trizma base (tris (hydroxymethyl)-aminomethane), sodium II phosphate, potassium hydroxide, or barium hydroxide to the aqueous solution containing the source material. In particular, ammonia solution is preferable.

For the aforementioned treatment, the following concentration of each solution may be used: approximately 0.01 to 15 N, preferably approximately 0.1 to 3 N, for ammonia or amino compound; approximately 0.01 to 2 N, preferably approximately 0.05 to 1 N, for sodium hydroxide; approximately 1 mM to 1 M, preferably approximately 20 mM to 200 mM, for trizma base; approximately 1 mM to 1 M, preferably approximately 10 mM to 100 mM, for sodium II phosphate; approximately 0.01 to 4 N, preferably approximately 0.1 to 2 N, for potassium hydroxide. The reaction temperature may be between approximately −20 to 80° C., and preferably between approximately −10 to 50° C.

The reaction time for S-cyanation reaction may be approximately 1 to 60 min., preferably approximately 15 to 30 min.; for hydrolysis reaction, approximately 5 min. to 100 hours, preferably approximately 10 min. to 15 hours; and for ammonolysis, approximately 5 min. to 24 hours, preferably approximately 10 to 180 min.

The aforementioned amino compound includes a compound represented by the formula $R^1$—$(NR^2)$—H, wherein $R^1$ and $R^2$ may be the same or different, and indicate (i) a hydrogen atom; (ii) $C_{1-20}$ alkyl group, $C_{3-8}$ cycloalkyl group, $C_{6-14}$ aryl group, or $C_{6-14}$ aryl-$C_{1-3}$ alkyl group (these may have no substituent groups, or may have 1 to 3 amino groups or hydroxyl groups on a carbon atom); (iii) substitutable amino groups; (iv) hydroxyl groups or $C_{1-6}$ alkoxy groups.

The reaction by the S-cyanation, and ammonolysis or hydrolysis may occur as indicated in FIG. 1.

As described above, the C-terminal of the KiSS-1 peptide obtainable by the producing method of the present invention may be amide (—$CONH_2$), carboxyl group (—COOH), carboxylate (—$COO^-$), alkylamide (—CONHR), or ester (—COOR). Amide, carboxyl group or alkylamide is preferable, and in particular, amide or alkylamide is suitable. Specifically, the C-terminal of the KiSS-1 peptide obtainable by the producing method of the present invention may be the —CO—X indicated in FIG. 1, wherein X indicates $R^1$—$(NR^2)$—($R^1$ and $R^2$ indicate the same meanings as above) or OH.

The aforementioned $C_{1-20}$ alkyl indicates, for examples, methyl, ethyl, propyl, isopropyl, butyl, sec-butyl, penthyl, isopenthyl, neopenthyl, 1-ethylpenthyl, hexyl, isohexyl, heptyl, octyl, nonanyl, decanyl, undecanyl, dodecanyl, tetradecanyl, pentadecanyl, hexadecanyl, heptadecanyl, octadecanyl, nonadecanyl, and eicosanyl.

The aforementioned $C_{3-8}$ cycloalkyl indicates, for examples, cyclopropyl, cyclobutyl, cyclopenthyl, cyclohexyl, cycloheptyl, and cyclooctyl.

The aforementioned $C_{6-14}$ aryl indicates, for examples, phenyl, naphthyl, anthryl, phenanthryl, and acenaphthylenyl.

The aforementioned $C_{6-14}$ aryl-$C_{1-3}$-alkyl indicates, for examples, benzyl, phenethyl, 3-phenylpropyl, (1-naphthyl) methyl, and (2-naphthyl)methyl.

The aforementioned $C_{1-6}$ alkoxy indicates, for examples, methoxy, ethoxy, propoxy, butoxy, penthyloxy, and hexyloxy.

Substituents for the substitutable amino groups described in (iii) above include amino acids, and peptides comprising 2 to 10 amino acids.

The above amino acids may be L-form or D-form, including Ala, Arg, Asp, Asn, Glu, Gln, Gly, His, Ile, Met, Leu, Lys, Phe, Pro, Ser, Thr, Trp, Tyr, and Val.

The above peptides include, for examples, H-D-Leu-Leu-Arg-Pro-NH-$C_2H_5$, and H-Val-Ala-Leu-D-Ala-Ala-Pro-Leu-Ala-Pro-Arg-OH.

In particular, it is preferred that $R^2$ is a hydrogen atom, and $R^1$ is a hydrogen atom or a $C_{1-20}$ alkyl group.

When using ammonia or an amino compound in the ammonolysis reaction, the corresponding amide form is obtained.

Conventional peptide purification methods may be used to isolate the excised target peptide. An appropriate combination of, for example, gel filtering, ion-exchange chromatography, absorption chromatography, high speed liquid chromatography, affinity chromatography, hydrophobic chromatography, thin layer chromatography or electrophoresis may be used.

The KiSS-1 peptide or salt thereof obtained in this way may also be isolated and purified from the reaction solution by well-known purification technique, for example, extraction, salting out, distribution, re-crystallization, or chromatography. The preferable purification method is ion-exchange chromatography via SP-sepharose (Pharmacia Biotech, Co., Ltd.), DEAE-5PW (Tosoh Co., Ltd.), or SP-5PW (Tosoh Co., Ltd.), etc.

The KiSS-1 peptide or salt thereof thus obtained may be lyophilized to form a powder if necessary. In lyophilization, stabilizers such as sorbitol, mannitol, dextrose, maltose, trehalose, or glycerol may be added.

The KiSS-1 peptide or salt thereof produced by the method of the present invention may be formulated with sterilized water, human serum albumin (HSA), physiological saline and other well-known physiologically acceptable carriers, and then may be administered to mammals (e.g., a human) parenterally or locally. For example, a daily dose per person of approximately 0.01 to 50 mg, preferably approximately 0.1 to 10 mg, may be administered parenterally by intravenous or intramuscular injection.

Compositions containing the KiSS-1 peptide or salt thereof produced by the method of the present invention may further contain other physiologically acceptable active components, such as a salt, diluent, adjuvant, other carriers, buffers, binders, surfactants, and preservatives. Parenteral dosage formulations may be provided as an ampoule of a suspension with a sterilized water solution or physiologically acceptable solvent, or as an ampoule of sterilized powder (normally obtained by lyophilization of the peptide solution) which can be diluted with a physiologically acceptable diluent at use.

The KiSS-1 peptide or salt thereof produced by the method of the present invention has an activity of inhibiting tumor metastasis, and is therefore useful as a prophylactic or therapeutic drug for all kinds of cancers (for example, lung cancer, stomach cancer, liver cancer, pancreatic cancer, colorectal cancer, rectal cancer, colon cancer, prostate cancer, ovarian cancer, uterine cancer, or breast cancer, etc.).

In addition, the KiSS-1 peptide or salt thereof has an activity of controlling placenta function, and is therefore useful as a prophylactic or therapeutic drug for choriocarcenoma, hydatid mole, invasive mole, miscarriage, fetal maldevelopment, saccharometabolic disorder, lipidosis, or induction of delivery.

In the present specification and drawings, codes of amino acids, peptides, protecting groups, active groups, and other substances are denoted on the base of the IUPAC-IUB (Commission on Biochemical Nomenclature) or conventional codes used in the related field. Examples are shown below. In addition, when amino acids can have optical isomers, unless specifically noted, the L-form is indicated.

| | |
|---|---|
| DNA | Deoxyribonucleic acid |
| A | Adenine |
| T | Thymine |
| G | Guanine |
| C | Cytosine |
| RNA | Ribonucleic acid |
| EDTA | Ethylene diamine tetra acetic acid |
| Gly | Glycine |
| Ala | Alanine |
| Val | Valine |
| Leu | Leucine |
| Ile | Isoleucine |
| Ser | Serine |
| Thr | Threonine |
| Met | Methionine |
| Glu | Glutamic acid |
| Asp | Aspartic acid |
| Lys | Lysine |
| Arg | Arginine |
| His | Histidine |
| Phe | Phenylalanine |
| Tyr | Tyrosine |
| Trp | Tryptophan |
| Pro | Proline |
| Asn | Asparagine |
| Gln | Glutamine |
| Cys | Cysteine |
| Asx | Asparagine or aspartic acid |
| Glx | Glutamine or glutamic acid |
| ATP | Adenosine triphospate |

The SEQ ID NO. in the Sequence Listing indicates the following sequence.

[SEQ ID NO: 1]
This sequence shows the amino acid sequence of the KiSS-1 peptide.

[SEQ ID NO: 2]
This sequence shows the nucleic acid sequence of the DNA encoding the KiSS-1 peptide.

[SEQ ID NO: 3]
This sequence shows the amino acid sequence of bFGF CS23 mutein.

[SEQ ID NO: 4]
This sequence shows a nucleic acid sequence of a DNA fragment encoding a fusion protein represented by formula (I).

[SEQ ID NO: 5]
This sequence shows a nucleic acid sequence of a DNA fragment encoding a fusion protein represented by formula (I).

[SEQ ID NO: 6]
This sequence shows the nucleic acid sequence of a DNA fragment encoding a bFGF CS23 mutein fragment.

[SEQ ID NO: 7]
This sequence shows a nucleic acid sequence of an oligomer used for preparing the structural gene of the KiSS-1 peptide in Example 1.

[SEQ ID NO: 8]
This sequence shows a nucleic acid sequence of an oligomer used for preparing the structural gene of the KiSS-1 peptide in Example 1.

[SEQ ID NO: 9]
This sequence shows a nucleic acid sequence of an oligomer used for preparing the structural gene of the KiSS-1 peptide in Example 1.

[SEQ ID NO: 10]
This sequence shows a nucleic acid sequence of an oligomer used for preparing the structural gene of the KiSS-1 peptide in Example 1.

[SEQ ID NO: 11]
This sequence shows a nucleic acid sequence of an oligomer used for preparing the structural gene of the KiSS-1 peptide in Example 1.

[SEQ ID NO: 12]
This sequence shows a nucleic acid sequence of an oligomer used for preparing the structural gene of the KiSS-1 peptide in Example 1.

[SEQ ID NO: 13]
This sequence shows a nucleic acid sequence of an oligomer used for preparing the structural gene of the KiSS-1 peptide in Example 1.

[SEQ ID NO: 14]
This sequence shows a nucleic acid sequence of an oligomer used for preparing the structural gene of the KiSS-1 peptide in Example 1.

[SEQ ID NO: 15]

This sequence shows the amino acid sequence of the KiSS-1 peptide mature form.

The present invention will be described in more detail below by way of example, not of limitation, with reference to the following examples.

EXAMPLES

Example 1

Production of DNA Encoding a KiSS-1 Peptide
(a) Synthesis of DNA Fragments

The structural gene of a KiSS-1 peptide was prepared (FIG. 3) using eight different DNA fragments (#1, #4, #5, #8: Amersham Pharmacia Biotech Co.; #2, #3, #6, #7: Kikotek Co. (SEQ ID NOs.: 7 to 14)) shown in FIG. 2.

(b) Phophorylation of DNA Oligomers

The phophorylation of 5' terminals of the 6 oligomers (#2 to #7) (SEQ ID NO: 8 to 13), excluding #1 (SEQ ID NO: 7) and #8 (SEQ ID NO: 14), was conducted by incubating each DNA oligomer at 37° C. for one hour in 25 μL phophorylation reaction solution (DNA oligomer 10 μg, 50 mM tris-HCl, pH 7.6, 10 mM MgCl$_2$, 1 mM spermidine, 10 mM dithiothreitol (DTT), 0.1 mg/mL bovine serum albumin (BSA), 1 mM ATP, and 10 units T4 polynucleotide kinase (manufactured by Takara)). After doing phenol treatment, adding 2 times vol. of ethanol, and cooling to −70° C., the DNA was precipitated by centrifugation.

(c) Ligation of DNA Fragments

The DNA fragments thus obtained in a) above, #1 fragment, and #8 fragment were mixed to make 120 μl solution. After incubating this mixed solution at 90° C. for 10 min., annealing was conducted by cooling slowly to room temperature. The ligation was conducted using the TaKaRa DNA Ligation Kit ver. 2 (manufactured by Takara). After adding 30 μL of the Ligation Kit II solution to 30 μL of the annealing solution, then adding 60 μL Ligation Kit I solution, the ligation was conducted at 37° C. for one hour. After doing phenol treatment, adding 2 times vol. of ethanol to the aqueous layer recovered, and cooling to −70° C., the DNA was precipitated by centrifugation. The DNA fragment obtained in this way was phosphorylated using T4 polynucleotide kinase (manufactured by Takara) for the next (d) step.

Figure 4:
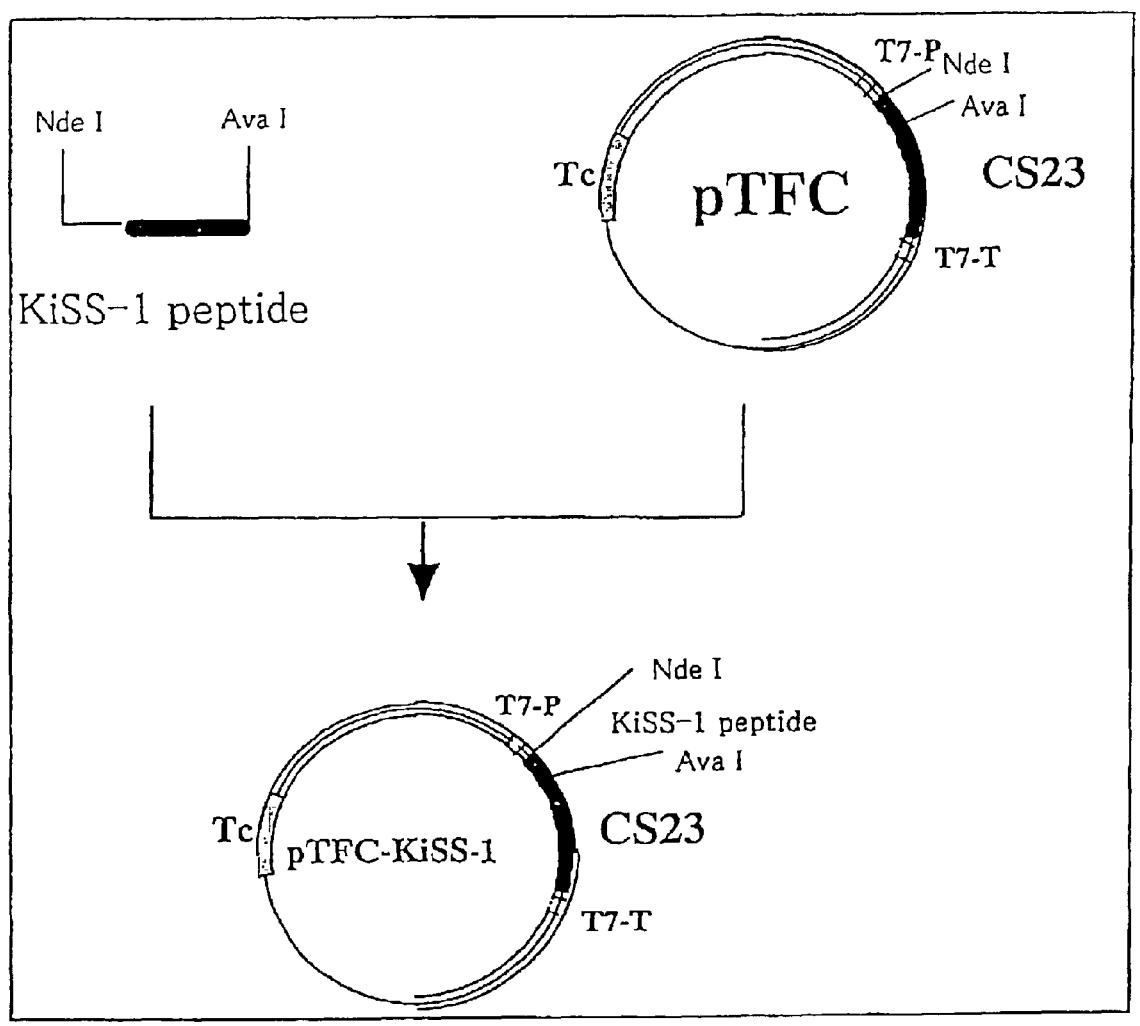
FIG. 4 indicates a schematic diagram of the construction of the plasmid pTFC-KiSS-1 obtained in Example 2.

(d) Construction of the Expression Vector for the KiSS-1 Peptide (FIG. 4)

To make the expression vector, pTFC (Publication of Patent Application: No.2000-270871, Patent Application: No.11-080303) was digested with NdeI and AvaI (manufactured by Takara) at 37° C. for four hours. After 1% agarose gel electrophoresis, 4.4 kb DNA fragment was extracted using the QIAquick Gel Extraction Kit (QIAGEN Co. ) and was dissolved in 25 μL. FE buffer solution. This NdeI/AvaI fragment of pTFC and the structural genes of the KiSS-1 peptides prepared as above were ligated using the TaKaRa DNA Ligation Kit ver. 2 (manufactured by Takara).

*Escherichia coli* JM109 competent cells (Toyobo Co.) were transformed with 10 μL of the ligation solution, inoculated on an LB agar medium containing 10 μg/mL tetracycline. After cultured overnight at 37° C., tetracycline resistant colonies were selected. These transformants were cultured overnight at 37° C. in LB medium, and plasmid pTFC-KiSS-1 was prepared using the QIAprep8 Miniprep Kit (QIAGEN Co.). The nucleic acid sequence of this KiSS-1 structural gene partion was confirmed using the Applied Biosystems Co. Model 377 DNA sequencer. *Escherichia coli* MM294 (DE3) was transformed with plasmid pTFC-KiSS-1, and a strain which can express KiSS-1 peptide-CS23 fusion protein, M294(DE3)/pTFC-KiSS-1, was obtained (FIG. 4).

*Escherichia coli* MM294(DE3)/pTFC-KiSS-1 was deposited at the National Institute of Bioscience and Human-Technology, AIST, MITI on Oct. 4, 1999, as the deposit No. FERM BP-6907. This was also deposited at the Institute for Fermentation, Osaka (IFO) on Sep. 16, 1999, as the deposit No. IFO 16321.

(d) Production of KiSS-1 Peptide

MM294(DE3)/pTFC-KiSS-1 was cultured with shaking in 1 L of LB medium (1% peptone, 0.5% yeast extract, 0.5% sodium chloride) containing 5.0 mg/L tetracycline in a 2-L flask at 37° C. for 8 hours. The culture obtained was transferred to a 50-L fermentor containing 19 L of a main fermentation medium (1.68% sodium monohydrogen phosphate, 0.3% potassium dihydrogen phosphate, 0.1% ammonium chloride, 0.05% sodium chloride, 0.025% magnesium sulfate, 0.02% defoaming agent, 0.00025% ferrous sulfate, 0.0005% thiamin hydrochloride, 1.5% glucose, and 1.5% casamino acid), and aeration and agitation was started at 30° C. When the turbidity of the culture solution reached 500 kleet, isopropyl-β-D-thiogalactopiranoside was added at a final concentration of 12 mg/L, and the cultivation was carried out for another 6 hours. After the cultivation was finished, approximately 600 g (wet weight) cells was obtained by centrifugation of the culture medium, and stored at −80° C.

Example 2

Three hundred milliliters of 10 mM EDTA (pH 6.0) solution was added to 100 g of the cells obtained in Example 1, and after ultrasonication (Branson Sonifier Model 450), the centrifugal separation was conducted (10,000 rpm, 60 min.). The supernatant was pooled, and the same operation was conducted again using the sediment. The pooled supernatant was adjusted to pH 6.0, and passed through an AF-Heparin Toyopearl 650M column (11.3 cm ID×13.5 cm L, Tosoh), which had been equilibrated with 50 mM phosphate buffer solution (pH 6.0), for absorption. After washing, the elution was made with a stepwise gradient from 0 to 100% B (B=50 mM phosphate buffer solution+2M NaCl, pH 6.0), and the fraction containing KiSS-1 peptide-CS23 fusion protein was obtained (the fraction at an elution time of approximately 100 min. in the 100-min. gradient elution). By concentrating the fraction with a Pellicon mini-cassette (Millipore Co.), and further concentrating it as adding 0.1 M acetic acid, the KiSS-1 peptide-CS23 fusion protein in 0.1 M acetic acid solution was obtained. After adding urea to the solution at a final concentration of 6 M, approximately 100 mg of DMAP-CN (1-cyano-4-diethylaminopyridinium tetrafluoroborate) was added, and incubated for 15 min. at room temperature for reaction. After completion of the reaction, the reaction solution was passed through a Sephadex G-25 column (46 mm ID×600 mm L, Pharmacia) equilibrated with 50 mM monopotassium phosphate. By elution with 50 mM monopotassium phosphate used for equilibration at a flow rate of 6 mL/min, the fraction containing the S-cyanized KiSS-1 peptide-CS23 fusion protein was obtained. By concentrating and desalting the fraction with a Pellicon mini-cassette (Millipore Co.), and a desalted solution of KiSS-1 peptide-CS23 fusion protein was obtained. After adding urea to this desalted solution at a final concentration of 6 M, 25% ammonia water was further added at a final ammonia concentration of 3 M, and this was incubated for 15 min. at room temperature for reaction. After the reaction was completed, the pH was adjusted to 6.0 with acetic acid to give KiSS-1 peptide (amide form). This reaction solution was passed through a Sephadex G-25 column (46 mm ID×600 mm L, Pharmacia) equilibrated with 50 mM monopotassium phosphate. By elution with 50 mM monopotassium phosphate used for equilibration at a flow rate of 6 mL/min, the KiSS-1 peptide (amide form) fraction was obtained. This fraction was passed through an SP-5PW (21.5 mm ID×150 mm L, Tosoh), which had been equilibrated with 50 mM MES containing 3 M urea, +3 M urea (pH 4.5), for absorption. After washing, the elution was made with a stepwise gradient from 0 to 30% B (B=50 mM phosphate buffer solution+1 M NaCl+3 M urea, pH 4.5), and the KiSS-1 peptide (amide form) fraction was obtained (the fraction at an elution time of approximately 30 min. in the 60-min. gradient elution). This fraction was further passed through a C4P-50 (21.5 mm ID×300 mm L, Showa Denko), which had been equilibrated with 0.1% trifluoroacetate, for absorption. After washing, the elution was made with a stepwise gradient from 20 to 50% B (B=80% acetonitrile/0.1% trifluoroacetate). The KiSS-1 peptide (amide form) fraction (the fraction at an elution time of approximately 45 min. in the 60-min. gradient elution) was pooled and lyophilized. Thus, approximately 40 mg powder of lyophilized KiSS-1 peptide (amide form) was obtained.

Example 3

Characterization of KiSS-1 Peptide a) Analysis of Amino Acid Composition

The amino acid composition was determined using an amino acid analyzer (Hitachi L-8500A). The result was consistent with the amino acid composition predicted from the DNA sequence of KiSS-1 peptide (Table 1).

TABLE 1

| Amino acid | Number of residues per mol | Value predicted from the DNA sequence of KiSS-1 peptide |
| --- | --- | --- |
| Asx | 3.5 | 4 |
| Thr[*] | 0.9 | 1 |
| Ser[*] | 7.3 | 8 |
| Glx | 7.0 | 7 |
| Pro | 8.1 | 8 |
| Gly | 4.9 | 5 |
| Ala | 2.9 | 3 |
| Cys | 0 | 0 |
| Val | 2.0 | 2 |
| Met | 0 | 0 |
| Ile | 0.9 | 1 |
| Leu | 5 | 5 |
| Tyr | 1.0 | 1 |
| Phe | 1.9 | 2 |
| His | 1.1 | 1 |
| Lys | 1.0 | 1 |
| Arg | 3.8 | 4 |
| Trp | 0.4 | 1 |

Acid hydrolysis (mean value after acid hydrolysis in 6N HCl-4% thioglycolic acid for 24–48 hrs)
[*]Value extrapolated at 0 hr.

b) Analysis of N-Terminal Amino Acid Sequence

The N-terminal amino acid sequence was determined using a gas phase protein sequencer (PE Applied Biosystems Model 492). The result was consistent with the N-terminal amino acid sequence predicted from the DNA sequence of KiSS-1 peptide (Table 2).

TABLE 2

| Residue No. | PTH[*]-amino acid detected | Amino acid predicted from the DNA sequence of KiSS-1 peptide |
| --- | --- | --- |
| 1 | Gly (28) | Gly |
| 2 | Thr (24) | Thr |
| 3 | Ser (12) | Ser |
| 4 | Leu (14) | Leu |
| 5 | Ser (9) | Ser |
| 6 | Pro (16) | Pro |
| 7 | Pro (17) | Pro |
| 8 | Pro (14) | Pro |
| 9 | Gln (7) | Gln |
| 10 | Ser (4) | Ser |
| 11 | Ser (6) | Ser |

100 pmol of the peptide was used.
[*]Phenylthiohydantoin c) Analysis of C-terminal Amino Acid The C-terminal amino acid was analyzed using an amino acid analyzer (Hitachi L-8500A), but the detection failed because the C-terminal was amide (Table 3).

TABLE 3

Analysis of C-terminal amino acid

| Kiss-1 peptide C-terminal amino acid | Recovery (%) |
| --- | --- |
| Phe | — |

Gas phase hydrazinolysis (100° C., 3.5 hrs)

Example 4

Measurement of Bioactivity

The activity of the human KiSS-1 peptide obtained in Example 2 was measured by the method described in Example 3 of WO 99/33976 (activity of increasing intracellular calcium ion concentration), confirming that the activity is equivalent to that of a standard product isolated from human placenta extract.

Example 5

Production of KiSS-1 Peptide (Non-Amide Form)

Three hundred milliliters of 10 mM EDTA (pH 6.0) solution was added to 100 g of the cells obtained in Example 1, and after ultrasonication (Branson Sonifier Model 450), the centrifugal separation was conducted (10,000 rpm, 60 min.). The supernatant was pooled, and the same operation was conducted again using the sediment. The pooled supernatant was adjusted to pH 6.0, and passed through an AF-Heparin Toyopearl 650M column (11.3 cm ID×13.5 cm L, Tosoh), which had been equilibrated with 50 mM phosphate buffer solution (pH 6.0), for absorption. After washing, the elution was made with a stepwise gradient from 0 to 100% B (B=50 mM phosphate buffer solution+2M NaCl, pH 6.0), and the fraction containing KiSS-1 peptide-CS23 fusion protein was obtained (the fraction at an elution time of approximately 100 min. in the 100-min. gradient elution). By concentrating the fraction with a Pellicon mini-cassette (Millipore Co.), and further concentrating it as adding 0.1 M acetic acid, the KiSS-1 peptide-CS23 fusion protein in 0.1 M acetic acid solution was obtained. After adding urea to the solution at a final concentration of 6 M, approximately 100 mg of DMAP-CN was added, and incubated for 15 min. at room temperature for reaction. After completion of the reaction, the reaction solution was passed through a Sephadex G-25 column (46 mm ID×600 mm L, Pharmacia) equilibrated with 50 mM monopotassium phosphate. By elution with 50 mM monopotassium phosphate used for equilibration at a flow rate of 6 mL/min, the fraction containing the S-cyanized KiSS-1 peptide-CS23 fusion protein was obtained. By concentrating and desalting the fraction with a Pellicon mini-cassette (Millipore Co.), and a desalted solution of KiSS-1 peptide-CS23 fusion protein was obtained. After adding urea to this desalted solution at a final concentration of 6 M, 1 N NaOH was further added at a final NaOH concentration of 0.05 N, and this was incubated for 15 min. at room temperature for reaction. After the reaction was completed, the pH was adjusted to 6.0 with acetic acid to give KiSS-1 peptide (non-amide form). This reaction solution was passed through a Sephadex G-25 column (46 mm ID×600 mm L, Pharmacia) equilibrated with 50 mM monopotassium phosphate. By elution with 50 mM monopotassium phosphate used for equilibration at a flow rate of 6 mL/min, the KiSS-1 peptide (non-amide form) fraction was obtained. This fraction was passed through an SP-5PW (21.5 mm ID×150 mm L, Tosoh), which had been equilibrated with 50 mM MES containing 3 M urea, +3 M urea (pH 4.5), for absorption. After washing, the elution was made with a stepwise gradient from 0 to 30% B (B=50 mM phosphate buffer solution+1 M NaCl+3 M urea, pH 4.5), and the KiSS-1 peptide (non-amide form) fraction was obtained (the fraction at an elution time of approximately 30 min. in the 60-min. gradient elution). This fraction was further passed through a C4P-50 (21.5 mm ID×300 mm L, Showa Denko), which had been equilibrated with 0.1% trifluoroacetate, for absorption. After washing, the elution was made with a stepwise gradient from 20 to 50% B (B=80% acetonitrile/0.1% trifluoroacetate). The KiSS-1 peptide (non-amide form) fraction (the fraction at an elution time of approximately 45 min. in the 60-min. gradient elution) was pooled and lyophilized. Thus, approximately 30 mg powder of lyophilized KiSS-1 peptide (non-amide form) was obtained.

Example 6

Characterization of KiSS-1 Peptide
a) Analysis of Amino Acid Composition

The amino acid composition was determined using an amino acid analyzer (Hitachi L-8500A). The result was consistent with the amino acid composition predicted from the DNA sequence of KiSS-1 peptide (Table 4).

TABLE 4

| Amino acid | Number of residues per mol | Value predicted from the DNA sequence of KISS-1 peptide |
|---|---|---|
| Asx | 3.3 | 4 |
| Thr[*] | 0.9 | 1 |
| Ser[*] | 7.0 | 8 |
| Glx | 7.0 | 7 |
| Pro | 7.8 | 8 |
| Gly | 4.7 | 5 |
| Ala | 2.8 | 3 |
| Cys | 0 | 0 |
| Val | 1.9 | 2 |
| Met | 0 | 0 |
| Ile | 0.9 | 1 |
| Leu | 5 | 5 |
| Tyr | 1.0 | 1 |
| Phe | 1.9 | 2 |
| His | 0.9 | 1 |

TABLE 4-continued

| Amino acid | Number of residues per mol | Value predicted from the DNA sequence of KISS-1 peptide |
|---|---|---|
| Lys | 0.9 | 1 |
| Arg | 3.7 | 4 |
| Trp | 0.4 | 1 |

Acid hydrolysis (mean value after acid hydrolysis in 6N HCl-4% thioglycolic acid for 24–48 hrs)
[*]Value extrapolated at 0 hr.

b) Analysis of N-Terminal Amino Acid Sequence

The N-terminal amino acid sequence was determined using a gas phase protein sequencer (PE Applied Biosystems Model 492). The result was consistent with the N-terminal amino acid sequence predicted from the DNA sequence of KiSS-1 peptide (Table 5).

TABLE 5

| Residue No. | PTH[*]-amino acid detected | Amino acid predicted from the DNA sequence of KiSS-1 peptide |
|---|---|---|
| 1 | Gly (17) | Gly |
| 2 | Thr (13) | Thr |
| 3 | Ser (11) | Ser |
| 4 | Leu (15) | Leu |
| 5 | Ser (8) | Ser |
| 6 | Pro (10) | Pro |
| 7 | Pro (11) | Pro |
| 8 | Pro (10) | Pro |
| 9 | Glu (5) | Glu |
| 10 | Ser (5) | Ser |

100 pmol of the peptide was used.
[*]Phenylthiohydantoin c) Analysis of C-Terminal Amino Acid The C-terminal amino acid was analyzed using an amino acid analyzer (Hitachi L-8500A) (Table 6).

TABLE 6

| Analysis of C-terminal amino acid | |
|---|---|
| Kiss-1 peptide C-terminal amino acid | Recovery (%) |
| Phe | 48.5 |

Gas phase hydrazinolysis (100° C., 3.5 hrs)

INDUSTRIAL APPLICABILITY

Using the producing method of the present invention, it is possible to manufacture in a large scale the peptide which can be used as a prophylactic or therapeutic drug for all kinds of cancers (for example, lung cancer, stomach cancer, liver cancer, pancreatic cancer, colorectal cancer, rectal cancer, colon cancer, prostate cancer, ovarian cancer, uterine cancer, or breast cancer, etc.) as well as for choriocarcenoma, hydatid mole, invasive mole, miscarriage, fetal maldevelopment, saccharometabolic disorder, lipidosis, or induction of delivery.

What is claimed is:

1. A method of producing a KiSS-1 peptide that contains the 47th to 54th residues from the N-terminal of the amino acid sequence represented by SEQ ID NO: 1 and consists of 8–54 amino acid of the amino acid sequence or a salt thereof, which comprises subjecting a fusion protein, polypeptide or salt thereof in which the a KiSS-1 peptide is ligated to the N-terminal of a protein or peptide having cysteine at the N-terminal, to the reaction of cleaving the peptide bond on the amino group side of said cysteine residue.

2. A method of producing a KiSS-peptide that contains the 47th to 54th residues from the N-terminal of the amino acid sequence represented by SEQ ID NO:1 and consists of 8–54 amino acids of the amino acid sequence or a salt thereof, which comprises expressing a fusion protein, polypeptide or a salt thereof in which the a KiSS-1 peptide is ligated to the N-terminal of a protein or peptide having cysteine at the N-terminal by culturing a transformant having a vector comprising DNA encoding the fusion protein or polypeptide; and subjecting the expressed fusion, polypeptide or the salt thereof to the reaction of cleaving the peptide bond on the amino group of said cysteine residue.

3. A producing method according to claim 1 or 2 wherein the C-terminal of the KiSS-1 peptide is an amide.

4. A producing method according to claim 1 or 2 wherein the cleavage reaction is S-cyanation reaction followed by an ammonolysis or hydrolysis reaction.

5. A producing method according to claim 1 or 2 wherein the KiSS-1 peptide is a peptide comprising an amino acid sequence represented by SEQ ID NO: 1.

6. A producing method according to claim 1 or 2 wherein the KiSS-1 peptide is (i) a peptide having the amino acid sequence from the 40th to 54th residues from the N-terminal of the amino acid sequence represented by SEQ ID NO: 1;

(ii) a peptide having the amino acid sequence from the 45th to 54th residues from the N-terminal of the amino acid sequence represented by SEQ ID NO: 1;

(iii) a peptide having the amino acid sequence from the 46th to 54th residues from the N-terminal of the amino acid sequence represented by SEQ ID NO: 1; or (iv) a peptide having the amino acid sequence from the 47th to 54th residues from the N-terminal of the amino acid sequence represented by SEQ ID NO: 1.

7. A producing method according to claim 1 or 2 wherein the protein or peptide having cysteine at the N-terminal is any of the following having cysteine at the N-terminal: interferon, interleukin, fibroblast growth factor, (pro) urokinase, lymphotoxin, tumor necrosis factor (TNF), β-galactosidase, storage proteins, streptoavidine, protein A, protein G, tissue plasminogen activator (TPA), or muteins or fragments thereof.

8. A producing method according to claim 1 or 2 wherein the protein or peptide having cysteine at the N-terminal is a protein or peptide that comprises an amino acid sequence represented by SEQ ID NO: 3 and has a cysteine residue added to the N-terminal.

9. A producing method according to claim 1 or 2 wherein the protein or peptide having cysteine at the N-terminal is a protein that has an amino acid sequence represented by SEQ ID NO: 1 and the KiSS-1 peptide to be produced is a peptide having an amino acid sequence represented by SEQ ID NO: 1; with an amide form of the C-terminal.

10. A fusion protein, polypeptide or salt thereof, in which a KiSS-1 peptide that contains the 47th to 54th residues from the N-terminal of the amino acid sequences represented by SEQ ID NO: 1 and consists of 8 to 54 amino acids of tho amino acid sequence is ligated to the N-terminal of a protein or peptide having cysteine at the N-terminal.

11. A fusion protein, polypeptide or a salt thereof according to claim 10, in which tho KiSS-1 peptide having the amino acid sequence represented by SEQ ID NO: 1 is ligated to the N-terminal of a protein comprising the amino acid sequence represented by SEQ ID NO: 3 and having a cysteine residue added to the N-terminal.

* * * * *

UNITED STATES PATENT AND TRADEMARK OFFICE
CERTIFICATE OF CORRECTION

PATENT NO. : 6,838,259 B2
DATED : February 28, 2005
INVENTOR(S) : Suenaga et al.

It is certified that error appears in the above-identified patent and that said Letters Patent is hereby corrected as shown below:

Column 25,
Line 28, after "KiSS" add -- -1 --
Line 55, delete "comprising" and insert therefor -- having --

Column 26,
Line 54, delete "tho" and insert therefor -- the --

Signed and Sealed this

Third Day of May, 2005

JON W. DUDAS
*Director of the United States Patent and Trademark Office*

SEQUENCE LISTING

<160> NUMBER OF SEQ ID NOS: 15

<210> SEQ ID NO 1
<211> LENGTH: 54
<212> TYPE: PRT
<213> ORGANISM: Human
<223> OTHER INFORMATION: the C-terminus of the polypeptide is amide
      (-CONH$_2$) form

<400> SEQUENCE: 1

Gly Thr Ser Leu Ser Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
                35                  40                  45

Ser Phe Gly Leu Arg Phe
        50              54

<210> SEQ ID NO 2
<211> LENGTH: 162
<212> TYPE: DNA
<213> ORGANISM: Human

<400> SEQUENCE: 2
ggtacttctc tgtctccgcc gccggaatct tctggttctc gtcagcagcc gggtctgtct      60
gctccgcact ctcgtcagat cccggctccg cagggtgctg ttctggttca gcgtgaaaaa     120
gacctgccga actacaactg gaactctttc ggtctgcgtt tc                        162

<210> SEQ ID NO 3
<211> LENGTH: 146
<212> TYPE: PRT
<213> ORGANISM: Human

<400> SEQUENCE: 3

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
                35                  40                  45

Pro His Ile Lys Leu Gln Leu Gln Ala Glu Glu Arg Gly Val Val Ser
    50                  55                  60

Ile Lys Gly Val Ser Ala Asn Arg Tyr Leu Ala Met Lys Glu Asp Gly
65                  70                  75                  80

Arg Leu Leu Ala Ser Lys Ser Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145

<210> SEQ ID NO 4
<211> LENGTH: 165
<212> TYPE: DNA
<213> ORGANISM: Human

<400> SEQUENCE: 4
ggtacttctc tgtctccgcc gccggaatct tctggttctc gtcagcagcc gggtctgtct      60
gctccgcact ctcgtcagat cccggctccg cagggtgctg ttctggttca gcgtgaaaaa     120
gacctgccga actacaactg gaactctttc ggtctgcgtt tctgc                     165

<210> SEQ ID NO 5
<211> LENGTH: 165
<212> TYPE: DNA
<213> ORGANISM: Human

<400> SEQUENCE: 5
ggtacttctc tgtctccgcc gccggaatct tctggttctc gtcagcagcc gggtctgtct      60
gctccgcact ctcgtcagat cccggctccg cagggtgctg ttctggttca gcgtgaaaaa     120
gacctgccga actacaactg gaactctttc ggtctgcgtt tctgt                     165

<210> SEQ ID NO 6
<211> LENGTH: 432
<212> TYPE: DNA
<213> ORGANISM: Human

<400> SEQUENCE: 6
cccgaggatg gcggcagcgg cgccttcccg cccggccact tcaaggaccc caagcggctg      60
tactgcaaaa acgggggctt cttcctgcgc atccaccccg acggccgagt tgacggggtc     120
cgggagaaga gcgaccctca catcaagcta caacttcaag cagaagagag aggagttgtg     180
tctatcaaag gagtgagcgc taatcgttac ctggctatga aggaagatgg aagattacta     240
gcttctaagt ctgttacgga tgagtgtttc ttttttgaac gattggaatc taataactac     300
aatacttacc ggtcaaggaa ataccaccagt tggtatgtgg cactgaaacg aactgggcag    360
tataaacttg gatccaaaac aggacctggg cagaaagcta tactttttct tccaatgtct     420
gctaagagct gc                                                         432

<210> SEQ ID NO 7
<211> LENGTH: 36
<212> TYPE: DNA
<213> ORGANISM: Artificial Sequence
<220> FEATURE:
<223> OTHER INFORMATION: Primer

<400> SEQUENCE: 7
tatgggtact tctctgtctc cgccgccgga atcttc                               36

<210> SEQ ID NO 8
<211> LENGTH: 45
<212> TYPE: DNA
<213> ORGANISM: Artificial Sequence
<220> FEATURE:
<223> OTHER INFORMATION: Primer

<400> SEQUENCE: 8
tggttctcgt cagcagccgg gtctgtctgc tccgcactct cgtca                     45

<210> SEQ ID NO 9
<211> LENGTH: 42
<212> TYPE: DNA

```
<213> ORGANISM: Artificial Sequence
<220> FEATURE:
<223> OTHER INFORMATION: Primer

<400> SEQUENCE: 9
gatcccggct ccgcagggtg ctgttctggt tcagcgtgaa aa                    42

<210> SEQ ID NO 10
<211> LENGTH: 47
<212> TYPE: DNA
<213> ORGANISM: Artificial Sequence
<220> FEATURE:
<223> OTHER INFORMATION: Primer

<400> SEQUENCE: 10
agacctgccg aactacaact ggaactcttt cggtctgcgt ttctgcc               47

<210> SEQ ID NO 11
<211> LENGTH: 46
<212> TYPE: DNA
<213> ORGANISM: Artificial Sequence
<220> FEATURE:
<223> OTHER INFORMATION: Primer

<400> SEQUENCE: 11
acgagaacca gaagattccg gcggcggaga cagagaagta cccata                46

<210> SEQ ID NO 12
<211> LENGTH: 45
<212> TYPE: DNA
<213> ORGANISM: Artificial Sequence
<220> FEATURE:
<223> OTHER INFORMATION: Primer

<400> SEQUENCE: 12
agccgggatc tgacgagagt gcggagcaga cagacccggc tgctg                 45

<210> SEQ ID NO 13
<211> LENGTH: 42
<212> TYPE: DNA
<213> ORGANISM: Artificial Sequence
<220> FEATURE:
<223> OTHER INFORMATION: Primer

<400> SEQUENCE: 13
cggcaggtct ttttcacgct gaaccagaac agcaccctgc gg                    42

<210> SEQ ID NO 14
<211> LENGTH: 41
<212> TYPE: DNA
<213> ORGANISM: Artificial Sequence
<220> FEATURE:
<223> OTHER INFORMATION: Primer

<400> SEQUENCE: 14
tcggggcaga aacgcagacc gaaagagttc cagttgtagt t                     41

<210> SEQ ID NO 15
<211> LENGTH: 145
<212> TYPE: PRT
<213> ORGANISM: Human

<400> SEQUENCE: 15

Met Asn Ser Leu Val Ser Trp Gln Leu Leu Leu Phe Leu Cys Ala Thr
1               5                   10                  15
```

-continued

```
His Phe Gly Glu Pro Leu Glu Lys Val Ala Ser Val Gly Asn Ser Arg
            20                  25              30

Pro Thr Gly Gln Gln Leu Glu Ser Leu Gly Leu Leu Ala Pro Gly Glu
            35                  40              45

Gln Ser Leu Pro Cys Thr Glu Arg Lys Pro Ala Ala Thr Ala Arg Leu
50                      55                  60

Ser Arg Arg Gly Thr Ser Leu Ser Pro Pro Pro Glu Ser Ser Gly Ser
65              70                  75                      80

Arg Gln Gln Pro Gly Leu Ser Ala Pro His Ser Arg Gln Ile Pro Ala
                85                  90              95

Pro Gln Gly Ala Val Leu Val Gln Arg Glu Lys Asp Leu Pro Asn Tyr
                100             105             110

Asn Trp Asn Ser Phe Gly Leu Arg Phe Gly Lys Arg Glu Ala Ala Pro
            115                 120             125

Gly Asn His Gly Arg Ser Ala Gly Arg Gly Trp Gly Ala Gly Ala Gly
            130             135             140

Gln
145
```